United States Patent [19] [11] 4,019,134
Hogg [45] Apr. 19, 1977

[54] PARTICLE DETECTOR INDEPENDENT OF ERRORS CAUSED BY CHANGES OF ELECTROLYTE CONDUCTIVITY AND ELECTRODE POLARIZATION

[75] Inventor: Walter R. Hogg, Miami Lakes, Fla.
[73] Assignee: Coulter Electronics, Inc., Hialeah, Fla.
[22] Filed: Mar. 11, 1976
[21] Appl. No.: 666,060

Related U.S. Application Data

[63] Continuation-in-part of Ser. No. 387,548, Aug. 13, 1973, Pat. No. 3,944,917.

[52] U.S. Cl. .............................. 324/71 CP; 324/64
[51] Int. Cl.² ....................................... G01N 27/00
[58] Field of Search ................ 324/71 CP, 30 R, 64

[56] References Cited

UNITED STATES PATENTS 3,745,455  7/1973  Haigh ............................ 324/71 CP
3,924,180  12/1975  Salzman et al. ................ 324/71 CP

OTHER PUBLICATIONS

Bebyakov, A.W., "Physicochemical Measurement," ..
USSR Journal – Izmeritel naya Tekhnika, No. 8, Aug., 1972, pp. 58–60.

Primary Examiner—Rudolph V. Rolinec
Assistant Examiner—Vincent J. Sunderdick
Attorney, Agent, or Firm—Silverman & Cass, Ltd.

[57] ABSTRACT

For use in a particle analyzer of the well known type, in which a microscopic aperture-defined sensing zone separates two bodies of electrolyte and particles in the electrolyte are caused to pass through the sensing zone; a first pair of sensing electrodes and a second pair of power electrodes are positioned with one electrode of each pair being on opposite sides of the aperture. A feedback circuit measures the constant D.C. voltage component between the sensing electrodes and feeds same back to the power electrodes, to cause the analyzer to be independent of power electrode polarization. The sensing electrodes are coupled to an output circuit, including a high input impedance voltage detecting amplifier, to enable the analyzer to operate accurately independent of changes in electrolyte conductivity. The connections to the sensing electrodes permit only negligible current to flow in them and thereby minimize their polarization.

18 Claims, 2 Drawing Figures

PARTICLE DETECTOR INDEPENDENT OF ERRORS CAUSED BY CHANGES OF ELECTROLYTE CONDUCTIVITY AND ELECTRODE POLARIZATION

CROSS REFERENCE TO RELATED APPLICATION

This application is a continuation-in-part of Ser. No. 387,548; filed Aug. 13, 1973, entitled "Electrical Sensing Circuitry For Particle Analyzing Device"; now U.S. Pat. No. 3,944,917, issued Mar. 16, 1976, and hereinafter cited as the "parent case".

To the extent that it may be necessary, U.S. Pat. No. 3,944,917 is incorporated herein.

BACKGROUND OF THE INVENTION

The present invention relates to electrical sensing circuitry for a particle analyzing device. The form of particle analyzing with which the teachings of the present invention are intended to be utilized first was disclosed in U.S. Pat. No. 2,656,508 and operates on a principle often now referred to as the Coulter principle. According to this principle, the passage of a microscopic particle suspended in a conducting liquid through an aperture having dimensions which approximate those of the particle, causes a change in the resistivity of the electrical path through the liquid effectively contained in the aperture. The magnitude of this change is proportional to the volume of the particle. The particle analyzing device typically includes a pair of electrodes positioned on either side of the aperture. An electrical power source is coupled to the electrodes and a signal detecting circuit is connected across the electrodes and usually includes an A.C. coupling, i.e. a D.C. blocking capacitor so that the signal detecting circuit will sense only changes caused by the passage of a particle through the aperture. These signals commonly are referred to as particle pulses and are fed from the amplifier to other electrical circuitry for the analysis of the pulse height and for counting the pulses.

Examples of particle analyzing devices having the structure and associated electrical circuitry described above can be found in products sold under the trademark COULTER which is a registered trademark U.S. Pat. No. 995,825, of Coulter Electronics, Inc. of Hialeah, Florida. Particle analyzing devices of this type also are described in many patents, for example: U.S. Pat. Nos. 2,869,078; 2,985,830; 3,015,775; 3,122,431, and 3,259,842.

The conductivity of the liquid in which the particles are suspended and which usually contains an electrolyte is a function of composition and temperature of the suspension and concentration of the electrolyte. A change in conductivity results in changing the calibration of the particle analyzing device, such that a given pulse amplitude would no longer be an accurate indication of the size of the particle generating the pulse. Various electrical sensing circuits have been proposed for providing some compensation for changes in electrolyte conductivity. Examples of these prior art circuits may be found in U.S. Pat. Nos. 3,259,842; and 3,706,030; Canadian Pat. No. 864,075; and Russian Pat. No. 274,474.

In the parent case the problems caused by changes in both the conductivity of the electrolyte and the diameter of the aperture are discussed, and several embodiments disclosed for reducing such problems. Another problem briefly mentioned is that of polarization of the power electrodes.

The parent case discloses use of separate pairs of electrodes. One such pair can be called the sensing electrodes and another pair the power electrodes. In some embodiments electrodes form a conducting cell. In none of the embodiments of the parent case is the combined problems of electrode polarization and electrolyte conductivity changes resolved by employing only two pairs of electrodes and a voltage sensing detecting amplifier.

The problem of electrode polarization and error causing polarization voltages long has been known, as evidenced by the teachings of U.S. Pat. No. 3,259,842, which resolved this problem by employing an infinite impedance aperture current source coupled to the one pair of electrodes which acted as both the power and sensing electrodes. It also used a detecting amplifier having a low input impedance at signal frequencies. Such prior art detecting amplifier has the disadvantage of being electronically noisy, a significant limitation in the field of particle detecting and analysis in which there would result poor signal to noise ratio.

SUMMARY OF THE INVENTION

In order simultaneously to minimize the prior art problems of less-than-ideal signal to noise ratio, electrode polarization and conductivity dependence in a particle analyzer, the present invention provides separate pairs of sensing and power electrodes. The sensing electrodes are coupled to an output circuit having high input impedance. The sensing electrodes are coupled by a feedback circuit to the power electrodes such that the voltage supplied to the power electrodes is responsive to the D.C. voltage component between the sensing electrodes. This combination results in independence of electrolyte resistivity or conductivity. Polarization of the power electrodes is compensated for by a feedback arrangement and does not induce measuring error. Moreover, the output and feedfack circuits permit only negligible current to flow in the sensing electrodes to minimize their polarization.

As employed hereinafter, the term "sensing zone" encompasses the sensing aperture structure through which the particles flow.

DESCRIPTION OF THE PREFERRED EMBODIMENTS

Figure 1:
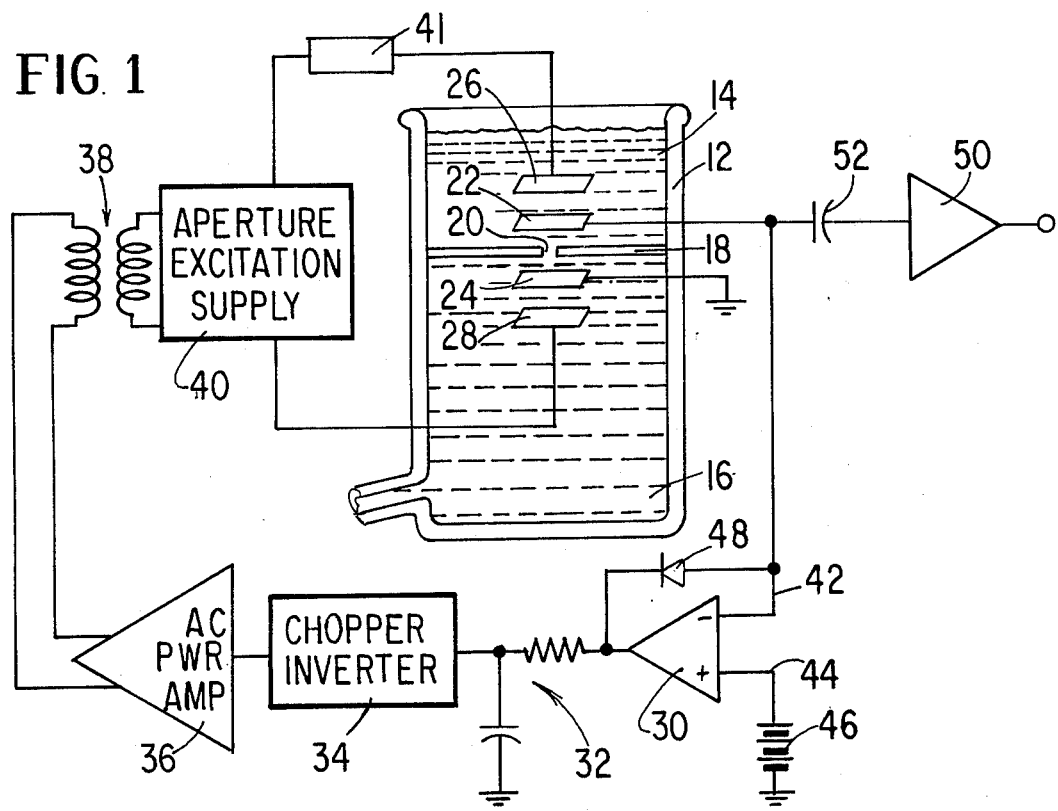
FIG. 1 is a schematic drawing of one embodiment of the invention.

FIG. 1 is very similar to FIG. 13 of the parent case, which embodiment is independent of changes in the diameter of the sensing aperture. As shown, the analyzing device includes a vessel 12, in which are contained two bodies of electrolyte 14 and 16 separated by a partition 18, in which there is situated a sensing aperture 20. A pair of sensing electrodes 22 and 24, and a pair of power electrodes 26 and 28 are provided. Although there will be polarization of the power electrodes 26 and 28, the effects of the resulting polarization voltages will be minimized by a feedback network comprising: a high input impedance isolation amplifier 30, an R.C. filter 32, a chopper inverter 34, a power amplifier 36, a transformer 38, an aperture excitation power supply 40, and an isolation impedance 41. The impedance 41 preferably would be infinite and could be the voltage-current characteristic of an electronically regulated current generator represented by the combination of the supply element 40 and the impedance 41.

As shown, one input 42 of the isolation amplifier 30 is connected to the sensing electrode 22 and the other input 44 of the isolation amplifier is connected to the positive side of a reference voltage 46, the other side of which is connected to ground, as is the other sensing electrode 24. In this circuit, the voltage between the sensing electrodes 22 and 24 is applied to the input 42 of the amplifier 30 and is compared with the reference voltage applied to the input 44 of the amplifier 30. If the voltages are different, an error signal will be produced by the amplifier 30. A diode 48 is connected between the input 42 and the output of the amplifier 30 to prevent runaway in the event that the voltage on the input 42 becomes more positive than on the input 44.

The A.C. component of the signal from the amplifier 30 is filtered out by the R.C. filter 32, leaving only the D.C. component, which then is converted into A.C. by the chopper inverter 34 and then is applied to the A.C. power amplifier 36. The A.C. power amplifier 36 applies A.C. power to the primary of the transformer 38, and the voltage induced in the secondary of the transformer is rectified and filtered in the aperture excitation power supply 40 to provide D.C. aperture excitation for the aperture 20. This feedback system reaches equilibrium when the voltage drop across the aperture 20, that is to say between the sensing electrodes 22 and 24, equals the voltage of the reference 46. Any voltages, such as those due to polarization, which appear on the power electrodes 26 and 28 will not effect the voltage across the aperture because these voltages are included in the feedback loop.

The resistances between the electrodes 22 and 26 on one side of the aperture and between the electrodes 24 and 28 on the other side are very small. However, the aperture excitation power supply 40 is large enough to force current through the power electrodes 26 and 28 and the voltage drop across the aperture 20 is picked up by the sensing electrodes 22 and 24. The resistance 41 serves to ensure that the aperture excitation power supply 40 has a high resistance at signal frequencies, to avoid shortcircuiting signal voltages appearing between electrodes 22 and 24.

Completing FIG. 1 is a signal detecting amplifier 50 having a high input impedance, and a capacitor 52 series coupled to the electrode 22. D.C. aperture current is prevented from flowing to the amplifier 50 by the capacitor 52, which is large enough to have a negligible reactance at signal frequencies. These two elements form an output circuit and the output from the detecting amplifier would be coupled to pulse analyzing apparatus, as is well known in the art, which would provide the desired data concerning the particles from which the pulses were derived.

By virtue of the fact that the capacitor 52 blocks the flow of D.C. current, combined with the fact that the transformer 38 has a high insulation resistance, there will be negligible current flowing in the sensing electrodes; hence, they will not be subject to polarization. Thus, the disclosed FIG. 1 embodiment resolves the problem of electrode polarization generically as well as specifically, with respect to the pairs of sensing and power electrodes.

Independence of changes in electrolyte conductivity is effected by ensuring that the aperture path current will vary inversely proportional to slow changes in aperture path resistivity, with voltage remaining constant; however, at the frequencies contained in the pulses due to the passing of particles through the aperture, the aperture current will remain constant, and particle-caused resistance changes in the aperture will generate detectable voltage signals. The parent case as well as Canadian Pat. No. 864,075 discuss this form of independence of conductivity, including mathematic derivations.

Figure 2:
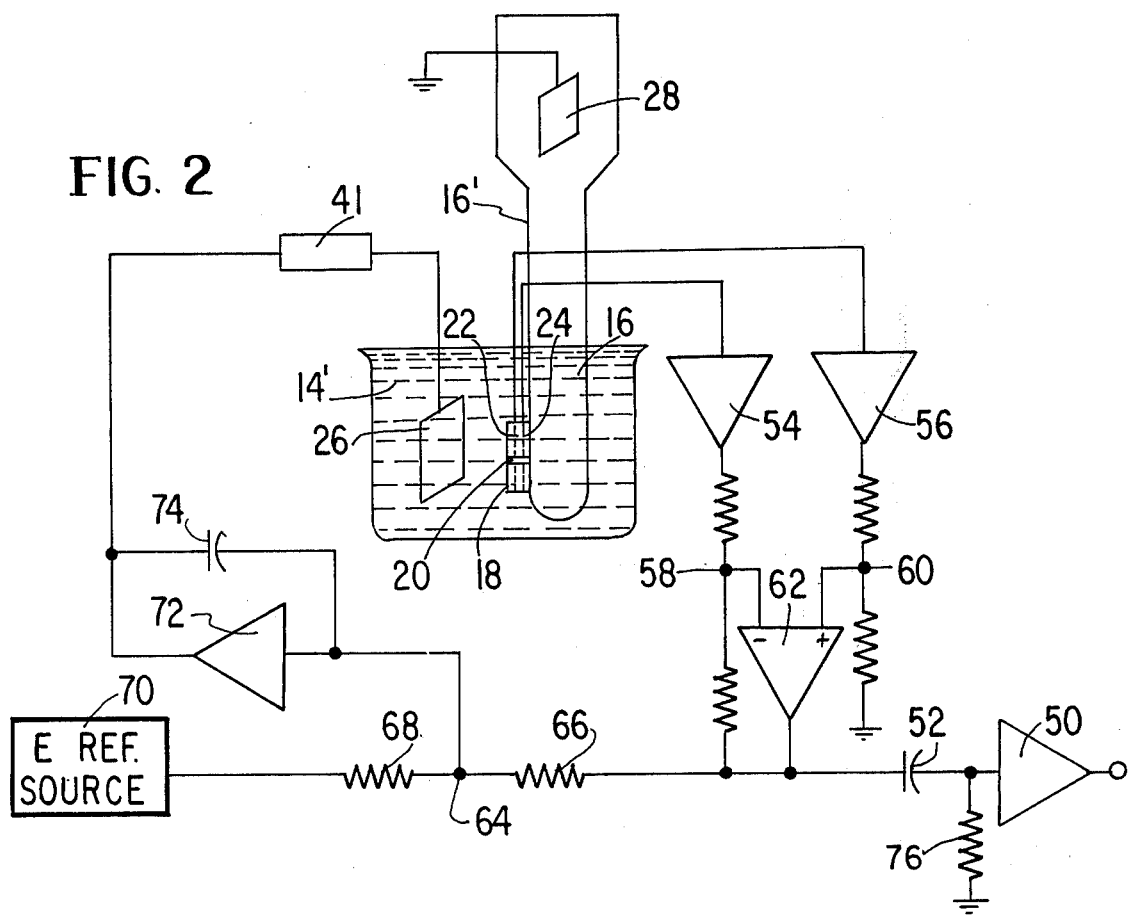
FIG. 2 is a schematic drawing of a second embodiment of the invention.

With respect to both of the embodiments in FIGS. 1 and 2, the following mathematic relationships should be appreciated. The aperture voltage $E_{ap}$ is the excitation source current $I_{ap}$ multiplied by the aperture resistance as measured between the sensing electrodes 22 and 24;

$$E_{ap} = I_{ap} R_{ap}. \qquad (1)$$

The change of resistance due to the passage of a particle through the aperture is $$\Delta R = (\rho v)/(A_0^2) \qquad (2)$$

and the aperture resistance is $$R_{ap} = (\rho l)/(A_0); \qquad (3)$$

wherein, $A_0$ is the cross-sectional area of the aperture normal to its axis, l is its effective length, $\rho$ is the electrolyte resistivity, and v is the volume of the particle. The open circuit voltage $e_{oc}$ developed by the change of resistance of the aperture is $$e_{oc} = I_{ap} \Delta R. \qquad (4)$$

Since the impedances of the detecting amplifier 50 and the aperture excitation supply 40 are many times higher than that of the aperture 20, there is negligible voltage divider action and the entire open circuit voltage is impressed upon the detecting amplifier 50.

Substituting the above values of $I_{ap}$, $\Delta R$, and $R_{ap}$ into equation (4):

$$e_{oc} = \frac{E_{ap} \Delta R}{R_{ap}} = \frac{E_{ap}}{\frac{\rho l}{A_0}} \cdot \frac{\rho v}{A_0^2} \qquad (5)$$

which simplifies to $$e_{oc} = \frac{E_{ap} v}{A_0^l}. \qquad (6)$$

Thus we have an expression for the open circuit voltage fed into the detecting amplifier; in which $\rho$, the resistivity of electrolyte, is missing. This confirms that the response of the embodied devices is independent of the resistivity or, conversely, the conductivity of the electrolyte.

It should be noted that in the FIG. 1 embodiment the sensing electrodes are not "floating" because the electrode 24 is grounded. Accordingly, it is possible to employ the single-ended input amplifier 50 which is quiet in its operation and permits the output circuit to be simple and not expensive. However, there then becomes a need for a floating power supply, as shown in FIG. 1 and hereinabove discussed. The reverse situation is shown in FIG. 2, with the sensing electrodes floating and the power supply being grounded.

Similar elements in FIGS. 1 and 2 carry the same reference numbers, even though the vessel-partition arrangement is illustrated in FIG. 2 in the more conventional form of an aperture tube 16' within a beaker 14'. The aperture 20 and the sensing electrodes 22 and 24 can be a laminated package mounted to the wall of the partition 18 to thereby allow the use of small sensing electrodes and a reduced sensing volume between these electrodes.

Since only negligible current is to flow in the sensing electrodes, they can be very remote from the aperture 20 with the power electrodes 26 and 28 closer to the aperture; hence, a mechanical but not electrical reversal of the positional arrangement shown in FIG. 1. Such a positional reversal will present a smaller gradient in the vicinity of the sensing electrodes, which can in all conditions of the present invention be quite small and thereby even less subject to polarization.

As shown in FIG. 2, buffer amplifiers 54 and 56 are connected, respectively to the sensing electrodes 22 and 24. These amplifiers have high input impedance for isolation and to prevent resistive loading of the sensing electrodes and thereby minimize current flow therein. These amplifiers would have small gain to avoid saturation and yet operate above their noise levels. The amplifiers are resistively coupled to the two inputs 58 and 60 of a differential amplifier 62. These three amplifiers and their resistive connections form a well known type of buffered subtractor, used herein as a circuit for receiving the voltage difference between the sensing electrodes 22 and 24, which are floating.

A summing junction 64 is coupled on one side to a resistor 66 and back to the output of the amplifier 62. The other side of the junction 64 is connected to a resistor 68 and a reference voltage source 70. These latter elements provide the comparator function, similar to that in FIG. 1. An operational amplifier 72 and capacitor 74 form an integrator, i.e. a low pass amplifier- filter, for feeding back the DC component of the derived error signal from the junction 64 to the isolation impedance 41, to complete the feedback loop to the power electrodes 26 and 28, the latter electrode being grounded. Of course, the A.C. particle-representing signals are resistance coupled to the amplifier 62, and to the amplifier 50 by way of the RC components 52 and 76.

It now should be apparent from the disclosed embodiments in FIGS. 1 and 2 that there has been provided a variable current aperture excitation supply at one end of the particle detector, and a voltage sensitive amplifier at the other end. The variable current supply has a high output resistance at signal frequencies and is controlled by means of the feedback arrangement in such a manner that the voltage across the aperture is held constant with respect to D.C. conditions, but the voltage is free to be changed in response to passing particles, i.e. at signal frequencies. In FIG. 2, the current excitation supply would be seen as the result of the voltage output from the integrator 72, 74 as applied to the very high impedance 41.

From the foregoing description and the appended claims, those skilled in the art will appreciate the scope and be able to practice the subject invention.

What is desired to be protected by United States Letters Patent is:

1. A particle detector for use with a particle analyzer having a microscopic particle sensing zone which separates two bodies of fluid, the particles being caused to pass from one body to the other via the sensing zone and thereupon enabling the generation of a discrete signal pulse related to each so passed particle, said detector comprising: a pair of power electrodes and a pair of particle sensing electrodes positioned in the bodies of fluid relative to the sensing zone such that a sensing electrode and a power electrode both are disposed in each of the bodies of fluid, voltage means for establishing a voltage between said particle sensing electrodes, such voltage having a D.C. component which is substantially constant, said voltage establishing means including feedback means coupling said sensing electrodes to said power electrodes for causing said particle detector to be substantially independent of power electrode polarization, and an output circuit including a high input impedance voltage sensitive detecting means coupled to said particle sensing electrodes for detecting the particle passing sensed by said sensing electrode and providing a pulse related to each passed particle in a manner such that said particle detector operates substantially independent of slow changes of conductivity in the bodies of fluid.

2. A particle detector according to claim 1 which includes a power supply coupled to said power electrodes, said power supply being constructed and arranged to be a floating supply and said particle sensing electrodes are coupled within the said particle detector to be non-floating.

3. A particle detector according to claim 1 which includes a variable current power supply coupled to said power electrodes and having a high output resistance at the frequencies of the passing particles.

4. A particle detector according to claim 1 which includes a power supply coupled to said power electrodes, said power supply being constructed and arranged to be a non-floating supply and said particle sensing electrodes are coupled within the said particle detector to be floating.

5. A particle detector according to claim 1 in which said feedback means comprises: voltage measuring means for measuring the voltage between said particle sensing electrodes, a source of reference voltage, comparing means for comparing said voltage between said particle sensing electrodes with said reference voltage and thereby generating an error signal, and a low pass amplifying means coupled between said voltage comparing means and said power electrodes.

6. A particle detector according to claim 5 in which said voltage measuring and comparing means is defined by the same electrical component.

7. A particle detector according to claim 1 in which said feedback means includes a pair of high input impedance buffer amplifiers connected to said pair of particle sensing electrodes for minimizing current flow in said particle sensing electrodes.

8. A particle detector according to claim 7 in which an amplifier is coupled to receive at separate inputs the respective outputs of said pair of buffer amplifiers, such three amplifiers being coupled to measure the voltage difference between said particle sensing electrodes.

9. A particle detector according to claim 7 wherein, in view of the minimal current flow in said particle sensing electrodes, they are positioned remote from the sensing zone.

10. A particle detector according to claim 1 in which said output circuit and said feedback means are constructed, arranged, and intercoupled to permit only negligible current to flow in the sensing electrodes.

11. A particle detector according to claim 10, wherein, in view of the negligible current flow in said particle sensing electrodes, they are positioned remote from the sensing zone.

12. A particle detector according to claim 10 in which said output circuit further includes a D.C. current blocking means coupled to said particle sensing electrodes, and said feedback means includes high resistance means.

13. A particle detector according to claim 12 in which said high resistance means is defined by a transformer having high insulation resistance.

14. A particle detector according to claim 13 in which a sensing zone excitation power supply is coupled to the output of said transformer.

15. A particle detector according to claim 14 in which high impedance means is interposed between said excitation power supply and said power electrodes.

16. A particle detector according to claim 15 in which said excitation power supply is a variable current supply having a high output resistance at the frequencies of the passing particles.

17. A particle detector according to claim 16 in which said excitation power supply is constructed and arranged to be a floating supply and said particle sensing electrodes being arranged to be non-floating.

18. A particle detector according to claim 17 in which said voltage sensitive detecting means comprises a single-ended input amplifier.

* * * * *

UNITED STATES PATENT AND TRADEMARK OFFICE
CERTIFICATE OF CORRECTION

PATENT NO. : 4,019,134
DATED : April 19, 1977
INVENTOR(S) : Walter R. Hogg

It is certified that error appears in the above-identified patent and that said Letters Patent are hereby corrected as shown below:

Column 1, lines 44-45, after "trademark" omit "U.S. Pat. No.".

Column 1, line 59, change "various" to -- Various -- (capitalize).

Column 2, line 40, change "feedfack" to -- feedback --.

Signed and Sealed this fifth Day of July 1977

[SEAL]

Attest:

RUTH C. MASON
Attesting Officer

C. MARSHALL DANN
Commissioner of Patents and Trademarks